(12) United States Patent
Bhullar

(10) Patent No.: US 6,662,439 B1
(45) Date of Patent: Dec. 16, 2003

(54) LASER DEFINED FEATURES FOR PATTERNED LAMINATES AND ELECTRODES

(75) Inventor: Raghbir Singh Bhullar, Indianapolis, IN (US)

(73) Assignee: Roche Diagnostics Corporation, Indianapolis, IN (US)

( * ) Notice: Subject to any disclaimer, the term of this patent is extended or adjusted under 35 U.S.C. 154(b) by 0 days.

(21) Appl. No.: 09/411,940

(22) Filed: Oct. 4, 1999

(51) Int. Cl.$^7$ .............................................. H01R 43/00
(52) U.S. Cl. ......................... 29/825; 846/847; 204/294
(58) Field of Search .......................... 29/846, 825, 847, 29/830; 204/294

(56) References Cited

U.S. PATENT DOCUMENTS

| | | | |
|---|---|---|---|
| 4,081,653 A | 3/1978 | Koo et al. | .................. 219/121 |
| 4,131,484 A | 12/1978 | Caruso et al. | .................. 134/1 |
| 4,414,059 A | 11/1983 | Blum et al. | .............. 156/659.1 |

(List continued on next page.)

FOREIGN PATENT DOCUMENTS

| | | |
|---|---|---|
| EP | 0 480 703 A2 | 4/1992 |
| EP | 0 480 703 B1 | 3/1997 |
| EP | 0 875 754 | 11/1998 |
| JP | 56100451 | 8/1981 |
| JP | 5-31 5703 | 11/1993 |
| JP | 7-66499 | 3/1995 |
| JP | 7-290751 | 11/1995 |
| JP | 9-260697 | 10/1997 |
| JP | 10-52780 | 2/1998 |
| JP | 10-241992 | 9/1998 |
| JP | 10-275959 | 10/1998 |
| JP | 10-303444 | 11/1998 |
| JP | 11297890 | 10/1999 |
| JP | 2000-121594 | 4/2000 |
| WO | WO 91/02391 | 2/1991 |
| WO | 0 438 344 B1 | 8/1994 |
| WO | WO 95/22881 | 8/1995 |
| WO | WO 98/35225 | 8/1998 |
| WO | WO 98/49773 | 12/1998 |
| WO | WO 98/55856 | 12/1998 |
| WO | WO 99/13101 | 3/1999 |
| WO | WO 99/30152 | 6/1999 |
| WO | WO 99/45387 | 9/1999 |
| WO | WO 00/73778 | 12/2000 |
| WO | WO 00/73785 | 12/2000 |

OTHER PUBLICATIONS

Tender, L. et al., Electrochemical Patterning of Self–Assembled Monolayers onto Microscopic Arrays of Gold Electrodes Fabricated by Laser Ablation, *Langmuir*, 1996, 12, 5515–5518.

Tahhan, Isam, "Biocompatible Microstructuring of Polymers and Electrodes with an Excimer Laser", MEDICS Workshop 2000 Speakers Abstracts, 2 pp.

Sheppard, Jr. et al. "Electrical Conductivity Measurements Using Microfabricated Interdigitated Electrodes", *Anal. Chem.*, 1993, 65, 1199–1202.

Srinivisan R., et al. "Ultraviolet Laser Ablation of Organic Polymers", *Chem. Rev.*, 1989, 89, 1303–1316.

Zongyi, Q., et al. "Excimer Laser Patterning on Thin Polymer Surfaces for Electrochemical Gas Sensors", Polymer Physics Laboratory, Changchun Institute of Applied Chemistry, Chinese Academy of Sciences, Changchun, Peop. Rep. China., Proceedings of the International Conference on Lasers (1999) 21$^{st}$ (Abstract) 1pp.

*Primary Examiner*—Carl J. Arbes
(74) *Attorney, Agent, or Firm*—Jill L. Woodburn; Richard T. Knauer

(57) ABSTRACT

A method of making a patterned laminate includes ablating through a portion of a metallic layer with a laser, to form a pattern in the metallic layer, where the metallic layer is on and in contact with an insulating substrate. The patterned laminate may be patterned to form electrodes, and can be formed into an electrochemical sensor strip.

29 Claims, 6 Drawing Sheets

U.S. PATENT DOCUMENTS

| | | |
|---|---|---|
| 4,684,437 A | 8/1987 | Donelon et al. ............. 156/643 |
| 4,874,500 A | 10/1989 | Madou et al. ............... 204/412 |
| 4,897,173 A | 1/1990 | Nankai et al. |
| 5,018,164 A | 5/1991 | Brewer et al. ............... 372/109 |
| 5,104,480 A | 4/1992 | Wojnarowski et al. ...... 156/643 |
| 5,120,420 A | 6/1992 | Nankai et al. |
| 5,264,103 A | 11/1993 | Yoshioka et al. |
| 5,266,179 A | 11/1993 | Nankai et al. |
| 5,288,636 A | 2/1994 | Pollmann et al. |
| 5,334,279 A | 8/1994 | Gregoire ..................... 156/630 |
| 5,336,388 A | 8/1994 | Leader et al. ................ 204/406 |
| 5,382,346 A | 1/1995 | Uenoyama et al. |
| 5,390,412 A | 2/1995 | Gregoire ...................... 29/848 |
| 5,391,250 A | 2/1995 | Cheney, II et al. ......... 156/268 |
| 5,395,504 A | 3/1995 | Saurer et al. |
| 5,413,690 A | 5/1995 | Kost et al. ................... 204/403 |
| 5,414,224 A | 5/1995 | Adasko et al. .............. 174/262 |
| 5,426,850 A | 6/1995 | Fukutomi et al. ............. 29/848 |
| 5,437,999 A | 8/1995 | Diebold et al. |
| 5,451,722 A | 9/1995 | Gregoire ..................... 174/261 |
| 5,465,480 A | 11/1995 | Karl et al. |
| 5,496,453 A | 3/1996 | Uenoyama et al. |
| 5,508,171 A | 4/1996 | Walling et al. .......... 205/777.5 |
| 5,509,410 A | 4/1996 | Hill et al. |
| 5,512,489 A * | 4/1996 | Girault et al. |
| 5,575,930 A | 11/1996 | Tietje-Girault et al. ....... 216/65 |
| 5,576,073 A | 11/1996 | Kickelhain .................. 427/555 |
| 5,589,326 A | 12/1996 | Deng et al. ...................... 435/4 |
| 5,593,739 A | 1/1997 | Kickelhain .................. 427/555 |
| 5,628,890 A | 5/1997 | Carter et al. |
| 5,635,054 A * | 6/1997 | Girault et al. |
| 5,682,884 A | 11/1997 | Hill et al. |
| 5,708,247 A | 1/1998 | McAleer et al. |
| 5,739,039 A * | 4/1998 | Hugues et al. |
| 5,755,953 A | 5/1998 | Henning et al. |
| 5,758,398 A | 6/1998 | Rijnbeek et al. ............ 29/25.42 |
| 5,759,364 A | 6/1998 | Charlton et al. |
| 5,762,770 A | 6/1998 | Pritchard et al. ........... 204/403 |
| 5,773,319 A | 6/1998 | Chu et al. |
| 5,798,031 A | 8/1998 | Charlton et al. ............. 204/403 |
| 5,955,179 A | 9/1999 | Kickelhain et al. ......... 428/210 |
| 5,956,572 A | 9/1999 | Kidoguchi et al. |
| 5,965,001 A | 10/1999 | Chow et al. ................. 204/600 |
| 6,004,441 A | 12/1999 | Fujiwara et al. ............. 204/412 |
| 6,103,033 A | 8/2000 | Say et al. .................... 156/73.1 |
| 6,134,461 A | 10/2000 | Say et al. .................... 600/345 |
| 6,165,594 A | 12/2000 | Moh et al. ................... 428/207 |
| 6,175,752 B1 | 1/2001 | Say et al. .................... 600/345 |
| 6,258,229 B1 | 7/2001 | Winarta et al. .............. 204/403 |
| 6,287,451 B1 | 9/2001 | Winarta et al. ........... 205/777.5 |
| 6,299,757 B1 | 10/2001 | Feldman et al. ............. 205/775 |
| 6,309,526 B1 | 10/2001 | Fujiwara et al. ............. 204/403 |
| 6,338,790 B1 | 1/2002 | Feldman et al. ......... 205/777.5 |

* cited by examiner

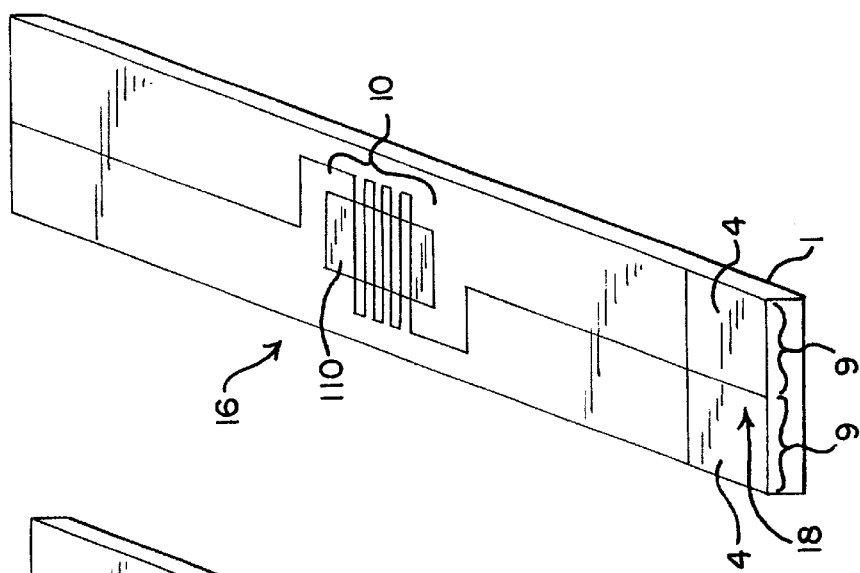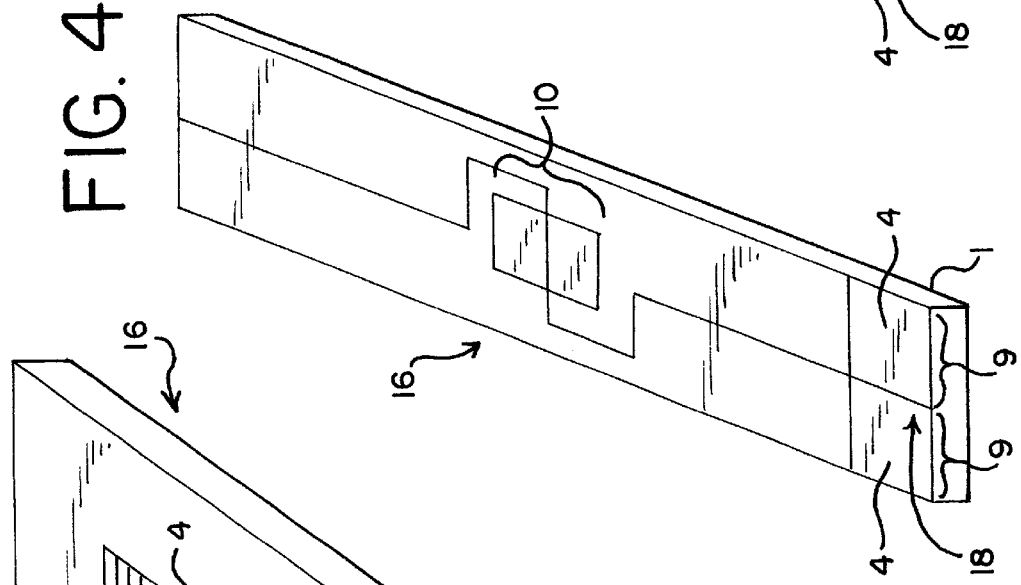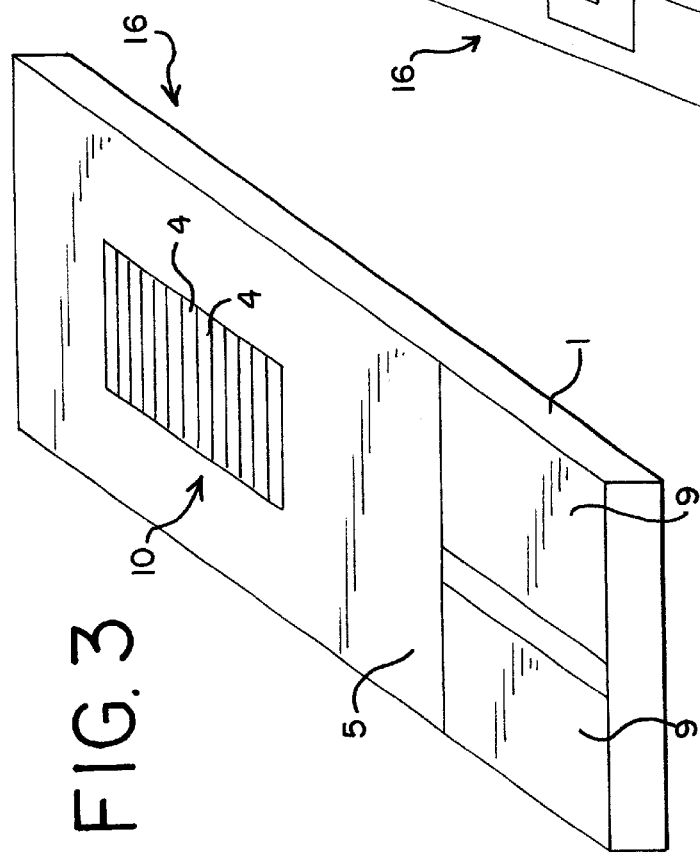

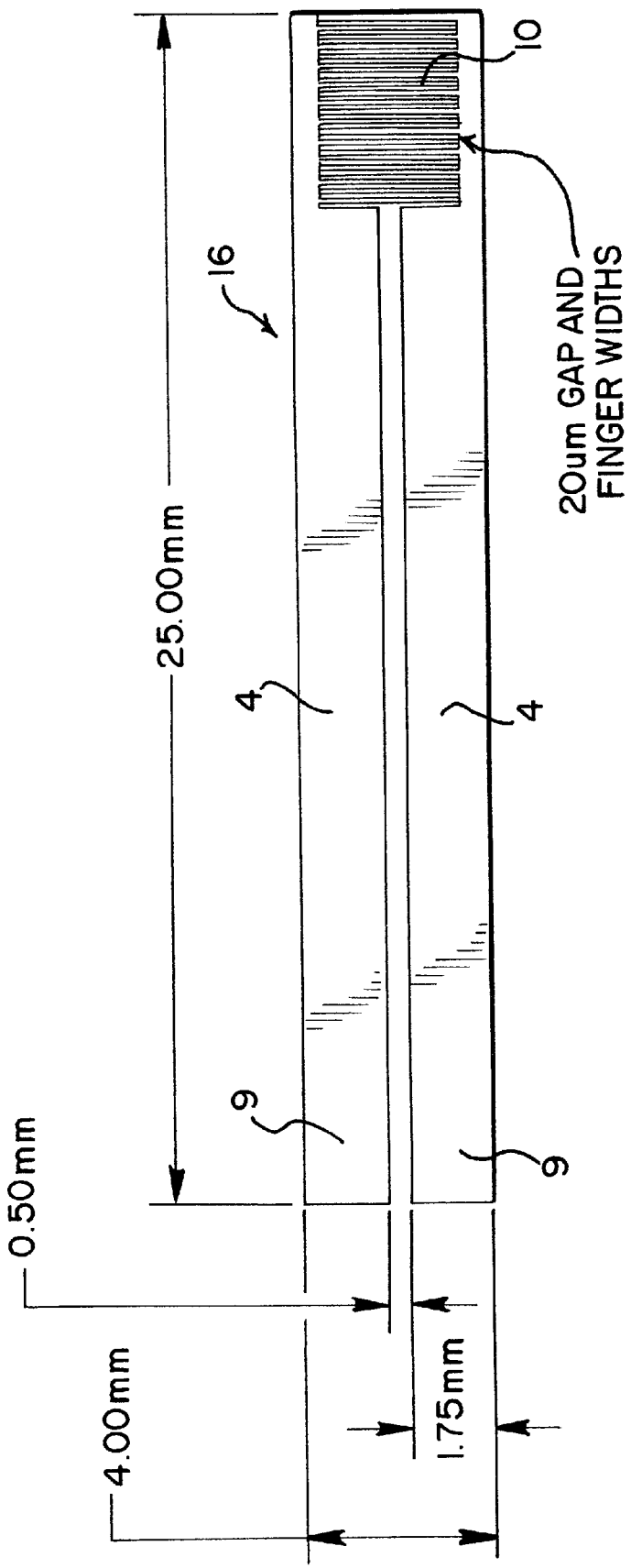

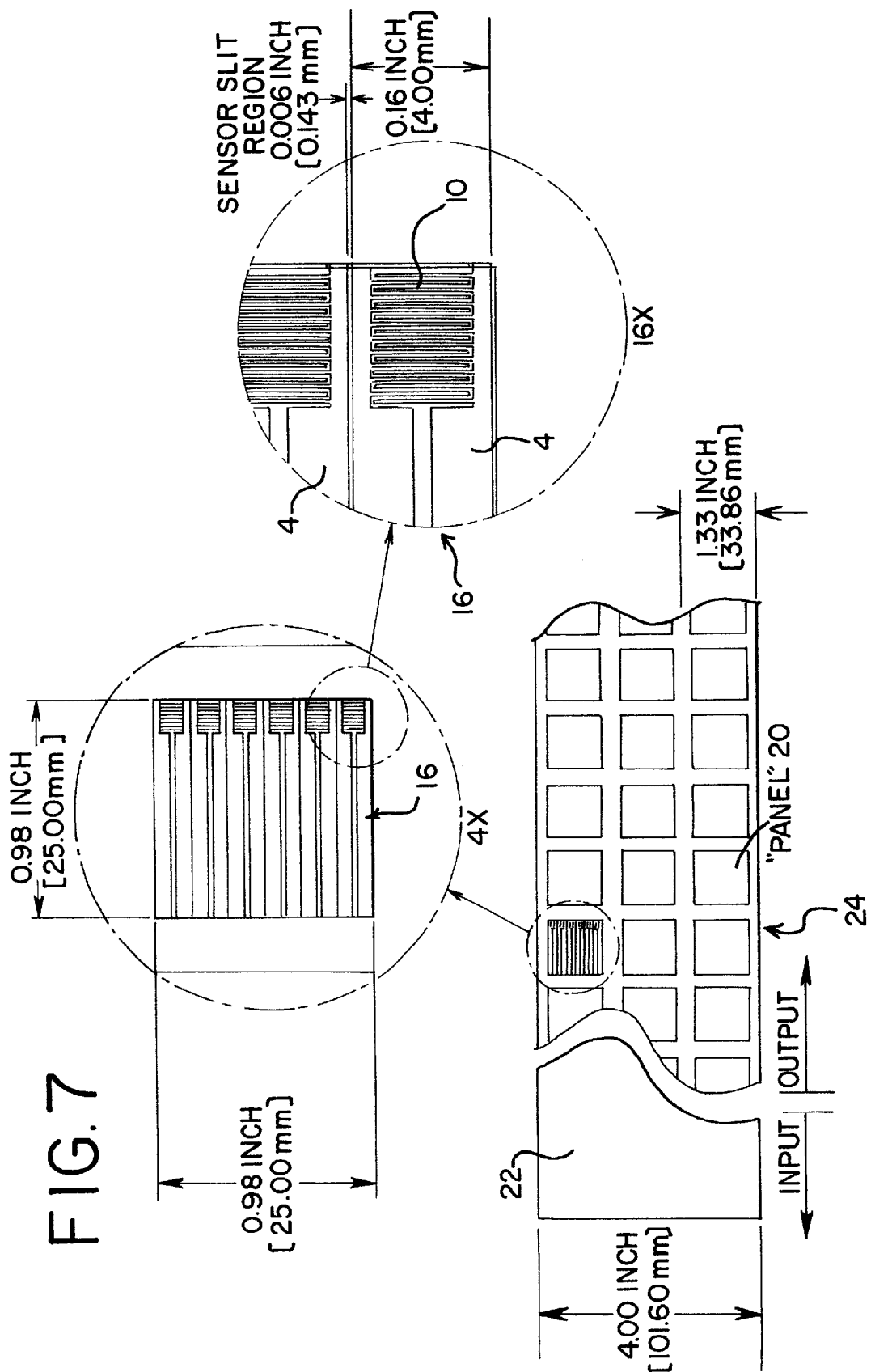

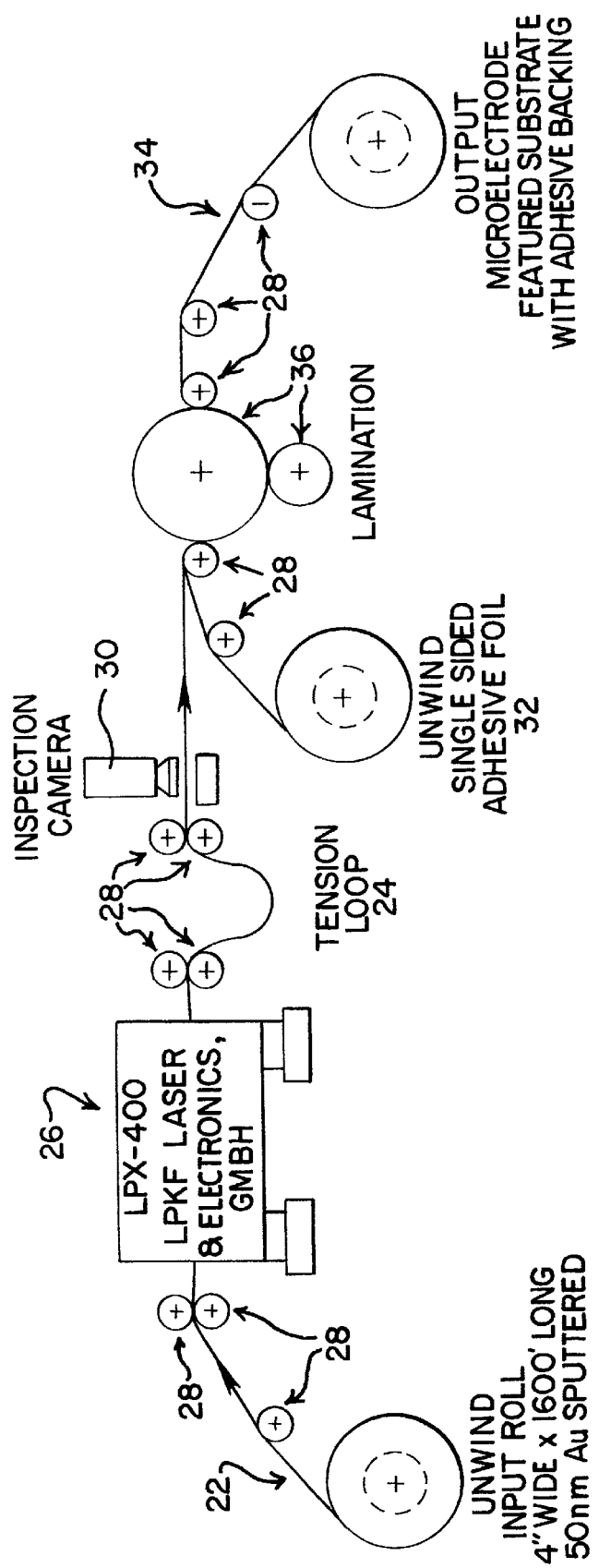

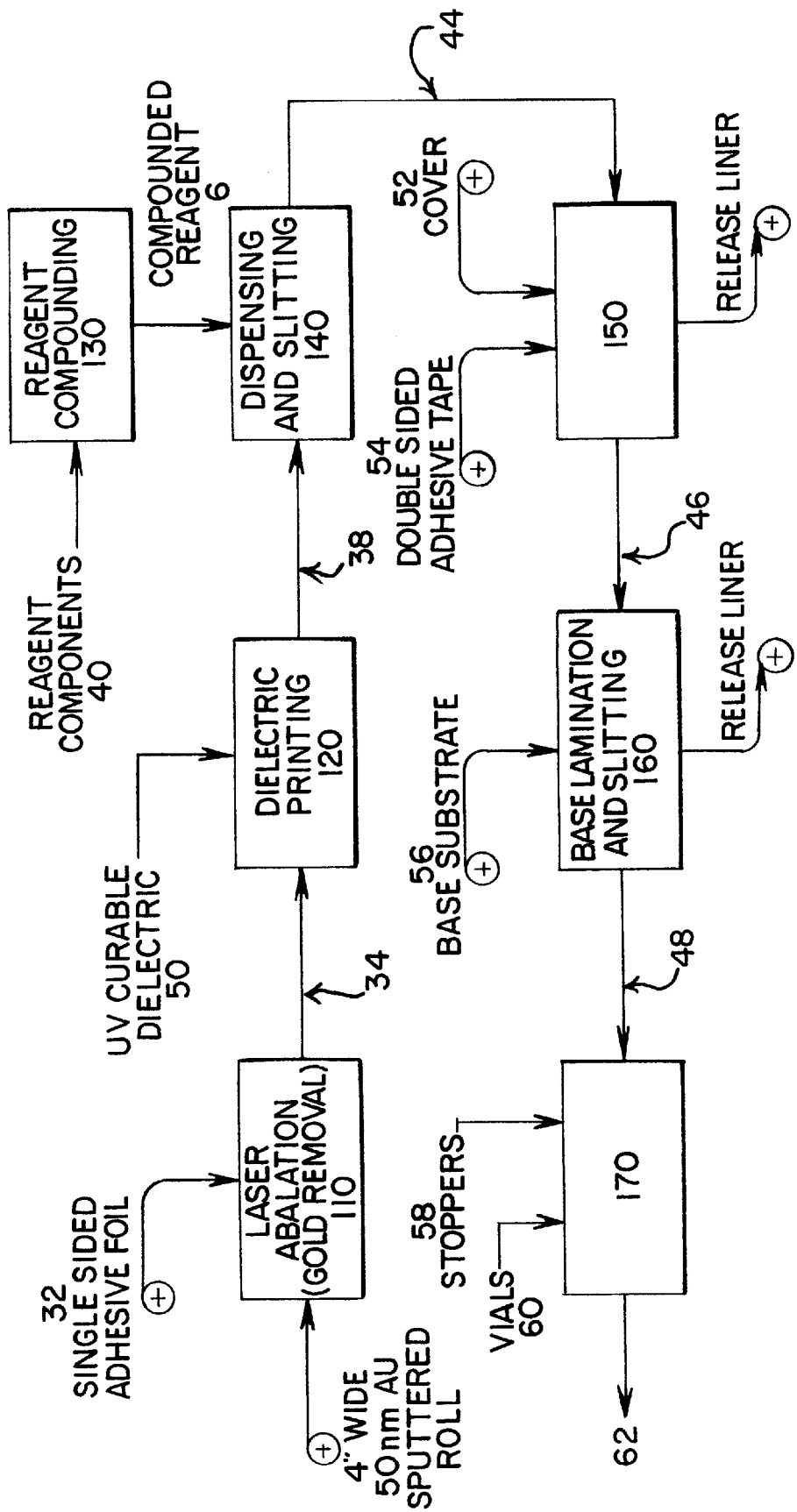

LASER DEFINED FEATURES FOR PATTERNED LAMINATES AND ELECTRODES

BACKGROUND OF THE INVENTION

The present invention relates to laser ablation to pattern a metallic layer, as well as an electrode for an electrochemical biosensor.

Electrochemical biosensors are well known. They have been used to determine the concentration of various analytes from biological samples, particularly from blood. Electrochemical biosensors are described in U.S. Pat. Nos. 5,413,690; 5,762,770 and 5,798,031; as well as in International Publication No. WO99/13101, each of which are hereby incorporated by reference.

An electrochemical biosensor typically includes a sensor strip. The sensor strip includes a space that holds the sample to be analyzed, may include reagents to be released into the sample, and includes an electrode set. The electrode set normally includes an insulating substrate, electrodes that contact the sample, which have contact pads for electrically connecting the electrodes to the electronics of electrochemical biosensor.

It is desirable for electrochemical biosensors to be able to analyze electrolytes using as small a sample as possible, and therefore it is necessary to miniaturize the sensor strip, as well as its parts, including the electrodes, as much as possible. Usually screen printing techniques have been used to form miniaturized electrodes.

Electrodes formed by screen printing techniques can only be formed from composition that are both electrically conductive and which are screen printable. Furthermore, screen printing techniques only allow for the reliable formation of structures and patterns having a feature size of approximately 75 µm or greater. In addition, screen printing is a wet chemical process. It would be desirable to have a new method of forming electrodes which allows for the use of different composition, and which can form features smaller than 75 µm.

Laser ablation is a technique using a laser to cut or mold a material. This technique usually uses a high power excimer laser, such as a krypton-fluoride excimer laser with an illumination wavelength of 248 nm, to blast away surface material. This technique has been used to ablate metals, polymers and even biological material, such as the cornea of the human eye. Such systems are well known to those of ordinary skill in the art, and are described in U.S. Pat. Nos. 5,576,073 and 5,593,739, each of which is hereby incorporated by reference.

SUMMARY OF THE INVENTION

In one aspect, the invention is a method of making a patterned laminate comprising ablating through a portion of a metallic layer with a laser. The metallic layer comprises at least one member of gold, platinum, palladium and iridium. Furthermore, the metallic layer is on, and in contact with, an insulating substrate, for example, a polymer.

In another aspect, the invention is a method of making a electrode set, comprising ablating through a portion of a first metallic layer with a laser, to form an electrode pattern. The first metallic layer is on an insulating substrate.

In still another aspect, the invention is a method of making an electrode set ribbon, comprising ablating through a portion of a first metallic layer with a laser, to form a plurality of electrode patterns. The first metallic layer is on an insulating substrate, for example, a polymer. The electrode set ribbon comprises a plurality of electrode sets.

In yet another aspect, the present invention is an electrode set, comprising a first metallic layer, on an insulating substrate, comprising a plurality of electrodes. The first metallic layer has a feature size of less than 75 µm.

In yet another aspect, the present invention is a patterned laminate, comprising a patterned metallic layer on, and in contact with, an insulating substrate. The metallic layer comprises at least one of gold, platinum, palladium and iridium. Furthermore, the insulating substrate comprises a polymer, and the patterned metallic layer has a feature size of less than 75 µm.

An advantage of the present invention is that it allows for the possibility of small feature sizes.

As used herein, the phrase "patterned laminate" means a multilayered structure that includes an overlayer through which an underlying layer is exposed, i.e. the overlayer has gaps and does not completely cover the underlying layer. The gaps or areas of exposure form the "pattern" of the patterned laminate. Furthermore, the term "pattern" means one or more intentionally formed gaps having a feature size, for example, a single linear gap having a constant width, where the smallest width is the feature size. Not included in the term "pattern" are natural, unintentional defects.

As used herein, the phrase "feature size" is the smallest dimension of a gap found in a pattern.

As used herein, the phrase "electrode pattern" is a pattern which when formed in a metallic layer includes at least two, for example 2 to 60, or 3 to 20, electrodes which are not electrically connected to each other, but each of which includes its own contact pad.

As used herein, the phrase "metallic layer" refers to a layer made of a material that is a metallic conductor of electricity, such as a pure metal or alloys.

As used herein, the phrase "electrode set" is a set of at least two electrodes, for example 2 to 60, or 3 to 20, electrodes. These electrodes may be, for example, a working electrode and a reference electrode.

As used herein, the phrase "ablating" means the removing of material.

Other objects, features and advantages of the present invention will become apparent from the following detailed description. It should be understood, however, that the detailed description and the specific examples, while indicating embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein:

FIG. 3 illustrates an electrode set of the present invention;

FIG. 4 illustrates another electrode set of the present invention;

FIG. 5 illustrates still another electrode set of the present invention;

FIG. 6 is a schematic of still another electrode set of the present invention;

FIG. 7 is a schematic of an electrode set ribbon of the present invention;

FIG. 8 is a schematic of a device of the present invention for making an electrode set ribbon of the present invention; and FIG. 9 is a block diagram of a process of the present invention for making a sensor strip of the present invention.

DETAILED DESCRIPTION OF THE INVENTION

Figure 1:
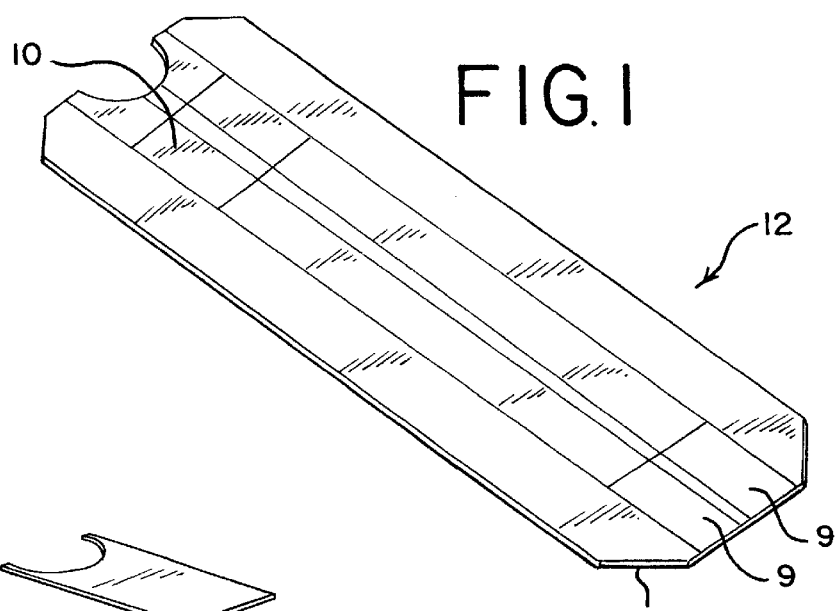
FIG. 1 illustrates an electrochemical sensor strip of the present invention.

FIG. 1 illustrates the assembled electrochemical sensor strip 12, which includes a base 1, the contact pads 9 and 9 that are part of the electrodes. The sensing region 10 of the electrodes is also illustrated.

Figure 2:
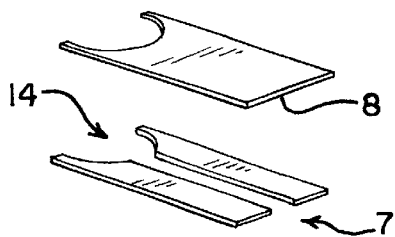
FIG. 2 illustrates an exploded view of an electrochemical sensor strip of the present invention, more clearing show each individual part.
Figure 2:
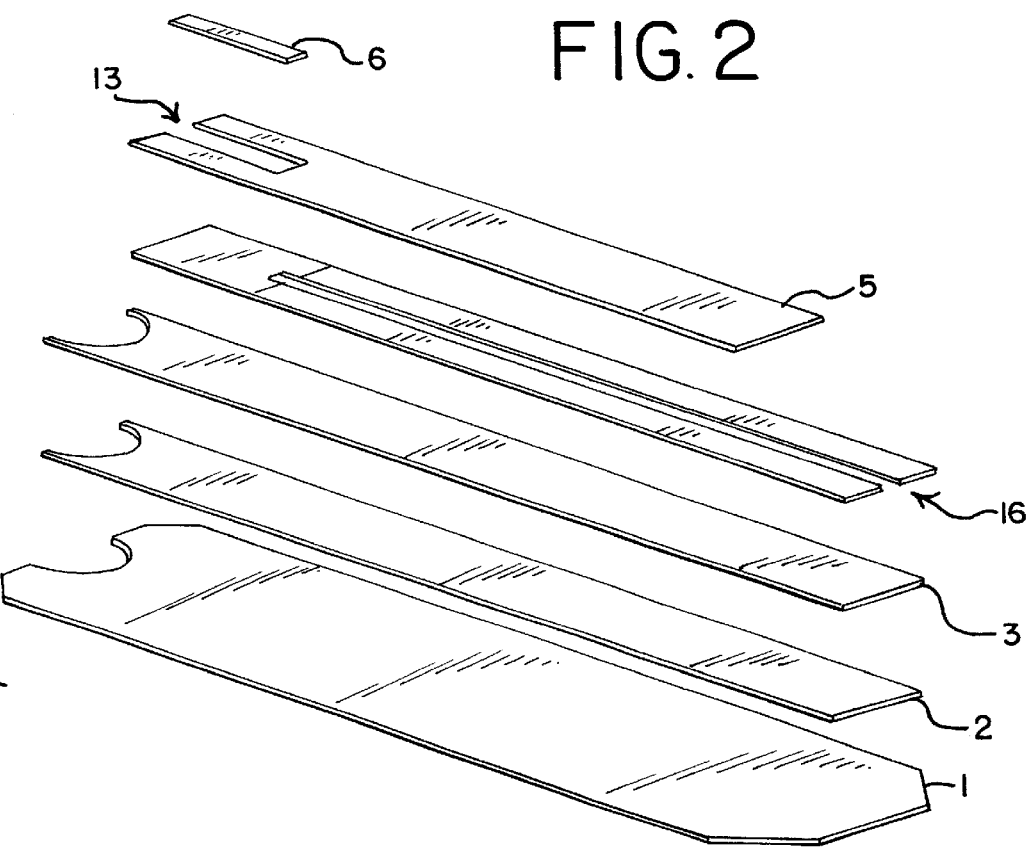

FIG. 2 illustrates an exploded view of a sensor strip 12, which includes a base 1, adhesive foil 2 for holding the base to the electrode substrate 3. The electrode set 16 is on the electrode substrate 3, and is partially covered by a dielectric 5. A cover 8 is attached to one end of the dielectric with adhesive tape 7. A small gap 13 in the dielectric, and a space 14 in the adhesive tape, together with the cover and the electrodes, form a pocket inside of which may be place reagent 6 used to aid in electrochemically detecting and quantifying an analyte. This pocket can act as a capillary, drawing the fluid to be tested onto the sensing region 10 (not shown) of the electrodes. Alternatively, the cover may be absent, exposing the sensing region of the electrodes, and the sample may be directly applied onto this region.

FIG. 3 illustrates an electrode set 16, including two electrodes 4 and 4. The electrodes have contact pads 9 and 9, which are electrically connected to the sensing region 10 of the electrode. Also illustrated is dielectric 5 which covers the first and second electrodes, exposing only the sensing region and the contact pads.

FIGS. 4 and 5 illustrate two different electrode sets 16, which each include a substrate 1, and first and second electrodes 4 and 4. The electrodes are separated by a gap 18 that prevents electrical contact between the two electrodes. For purposes of illustration, the regions of the electrodes which will become the sensing region 10, and the contact pads, 9 and 9, are shaded. The gap 18 corresponds to the feature size of this electrode set, since it is the smallest intentional feature. FIGS. 4 and 5 illustrate two different electrode patterns, one having a simple straight gap (FIG. 4), and the other more complex and containing a rectilinear gap, forming a region of interlacing fingers of the two electrodes (FIG. 5).

FIG. 6 is a schematic of an electrode set of the present invention, including two electrodes 4 and 4. The sensing region 10 of the electrodes contains interlacing fingers of the two electrodes, again a rectilinear gap. Also shown opposite the sensing region are the contact pads 9 and 9 of each electrode. The gap between the electrodes corresponds to the feature size, and may be 1 to 100 $\mu$m, preferably less than 75 $\mu$m, more preferably 5 to 50 $\mu$m, most preferably 10 to 30 $\mu$m. The gap passes completely through the metallic layer so that the two electrodes are not electrically connected in the electrode set. The values for the dimensions illustrated in FIG. 6 are for a single specific embodiment, and these values may be selected as need for the specific use. For example, the length of the electrode set may be 2.5 to 250 mm, the width may be 0.4 to 40 mm, the gap between the contact pads may be 1 $\mu$m to 5 mm, and the width of each contact pad may be 1to 20 mm. The electrode pattern shown in FIG. 6 (and other figures) is symmetric, however this is not required, and irregular or asymmetric patters (or electrode shapes) are possible.

FIG. 7 is a schematic of an electrode set ribbon 24. The ribbon includes a plurality of panels 20, each of which includes a plurality of electrode sets 16. Also shown is the original metallic laminate ribbon 22 that is subject to laser ablation to form the electrode set ribbon 24. The width of the ribbon is selected to accommodate the laser ablation system, and may be, for example, 40 to 0.4 inches. The ribbon may be any length, and is selected based on the desired number of electrode sets, and/or the ease of handling and transport of the ribbons. The size of each individual panel is selected to fit conveniently on the ribbon, and therefore each panel may contain 1 to 1000 electrode sets, preferably 2 to 20 electrode sets.

FIG. 8 is a schematic of a device for producing electrode sets, in the form of an electrode set ribbon 24. First a roll of metallic laminate ribbon 22 is fed through guide rolls 28 into a laser ablator 26. In the laser ablator the metallic layer of the metallic laminate ribbon is ablated with the laser, in an electrode pattern, to form the electrode set ribbon 24. The electrode set ribbon 24 is then passed through more guide rolls 28, with a tension loop to adjust the tension of the ribbon, and through an optional inspection camera 30, which may be used to check for defects. Next, optionally, the electrode set ribbon 24 may be laminated with an adhesive foil ribbon 32, in a laminator 36, to form a laminated electrode set ribbon 34, which is then guided through guide rolls 28, and rolled up.

FIG. 9 is a block diagram of a process for making an electrochemical sensor strip of the present invention. As shown, in step 110 the metallic laminate ribbon 22 is ablated by laser ablation to form an electrode set ribbon, and then laminated with adhesive foil ribbon 32 to form a laminated electrode set ribbon 34. In step 120 the laminated electrode set ribbon 34 is screen printed with a UV curable dielectric 50, which forms the dielectric 5 (not shown) of each sensor strip, forming a dielectric covered ribbon 38. In step 130 the starting reagents 40 are compounded to form reagent 6, and then in step 140 the reagent is applied onto the dielectric covered ribbon 38, the ribbon is split into reels, each one panel wide, to form reagent covered panel reels 44.

In step 150 the reagent covered panel reels 44 are covered with clear polyester roll 52 attach through double sided adhesive tape roll 54, which forms the clear cover 8 (not shown) and adhesive tape 7 (not shown) of each sensor strip. The product of step 150, clear covered panel reels 46, are then split into individual sensor reels, each one electrode set wide, and laminated with a base substrate roll 56, in step 160, which forms the base 1 (not shown) of each sensor strip, to form sensor reels 48. In step 170 the sensor reels are cut into individual sensor strips 12 (not shown) which are sorted and packed into vials 60, each closed with a stopper 58, to give packaged sensor strips 62. In steps 150 and 160, a liner is release in order to attach the base and cover.

A laser system capable of ablating the metallic layer, to form the individual electrode sets, is well known to those of ordinary skill in the art. Examples include excimer lasers, with the pattern of ablation controlled by lenses, mirrors or masks. An example of such a system is the LPX-400, or LPX-200, both from LPKF LASER ELECTRONIC, GMBH of Garbsen, Germany.

The metallic laminate is a metallic layer on the electrode substrate. The metallic layer may contain pure metals or alloys, or other materials which are metallic conductors. Examples include aluminum, carbon (such as graphite), cobalt, copper, gallium, gold, indium, iridium, iron, lead, magnesium, mercury (as an amalgam), nickel, niobium, osmium, palladium, platinum, rhenium, rhodium, selenium, silicon (such as highly doped polycrystalline silicon), silver, tantalum, tin, titanium, tungsten, uranium, vanadium, zinc, zirconium, mixtures thereof, and alloys or metallic compounds of these elements, Preferably, the metallic layer includes gold, platinum, palladium, iridium, or alloys of these metals, since such noble metals and their alloys are unreactive in biological systems. The metallic layer may be any thickness, but preferably is 10 nm to 1 mm, more preferably, 20 nm to 100 $\mu$m, or even 25 nm to 1 $\mu$m. FIG. 9 illustrates the process with a 50 nm gold film.

In the laser ablation process, the metallic layer may be ablated into an electrode pattern. Furthermore the patterned metallic layer may be coated or plated with additional metal layers. For example, the metallic layer may be copper, which is then ablated with a laser, into an electrode pattern; subsequently, the copper may be plated with a titanium/tungsten layer, and then a gold layer, to form the desired electrodes. Preferably, however, only a single layer of gold is used, which is directly in contact with the electrode substrate, since it allows for the entire elimination of wet chemical steps for the formation of the electrode sets.

The electrode substrate is formed from an insulating material, so that it will not provide an electrical connection between the electrodes of the electrode set. Examples include glass, ceramics and polymers. Preferably, the electrode substrate is a flexible polymer, such as a polyester or polyimide. An example of a suitable material would be the polyimide UPLEX from TECHNI-MET of Connecticut, which is available pre-coated with gold, palladium or platinum; or ULTEM 1000 (polyetherimide) from GE, available coated with copper. A UV curable dielectric and which is screen printable, may be used to form the dielectric, for example the polymer composition 5018 dielectric composition from DuPont. The clear cover is a clear material that is inert to biological fluids, for example glass, polyethylene, polypropylene, polyvinylchloride, polyimide, or polyester. The clear cover may have markings. The adhesive tape is also a flexible polymer having a surfaces covered with an adhesive; these materials are also well known to those of ordinary skill in the art.

The base is a supporting structure, and is preferably made of flexible polymer material, with a thickness sufficient to provide support to the sensor strip, for example polyester with a thickness of 6 mils. The adhesive foil may be made for the same types of compositions as the adhesive tape.

The reagent is optional, and may be used to provide electrochemical probes for specific analytes. The starting reagents are the reactants or components of the reagent, and are often compounded together in liquid form before application to the ribbons or reels. The liquid may then evaporate, leaving the reagent in solid form. The choice of specific reagent depends on the specific analyte or analytes to be measure, and are well known to those of ordinary skill in the art. For example, a reagent for measurement of glucose in a human blood sample contains 62.2 mg polyethylene oxide (mean molecular weight of 100–900 kilodaltons), 3.3 mg NATROSOL 250 M, 41.5 mg AVICEL RC-591 F, 89.4 mg monobasic potassium phosphate, 157.9 mg dibasic potassium phosphate, 437.3 mg potassium ferricyanide, 46.0 mg sodium succinate, 148.0 mg trehalose, 2.6 mg TRITON X-100 surfactant, and 2,000 to 9,000 units of enzyme activity per gram of reagent. The enzyme is prepared as an enzyme solution from 12.5 mg coenzyme PQQ and 1.21 million units of the apoenzyme of quinoprotein glucose dehydrogenase, forming a solution of quinoprotein glucose dehydrogenase. This reagent is described in WO 99/30152, pages 7–10.

The processes and products described include disposable biosensors, especially for use in diagnostic devices. However, also included are electrochemical sensors for non-diagnostic uses, such as measuring an analyte in any biological, environmental, or other, sample. Furthermore, also included is any patterned laminate, preferably a patterned laminate of a noble metal (gold, platinum, palladium, iridium, alloys thereof) in direct contact with an insulating substrate, such as a polymer. Such laminates can have a variety of electrical function, including use as electrodes, electrical wires or connectors, microwave reflectors, etc. Preferably, these patterned laminates have a feature size of 100 $\mu$m or less, more preferably 1 to 100 $\mu$m, even more preferably 75 $\mu$m or less, including 5 to 50 $\mu$m, or even 5 to 20 $\mu$m.

What is claimed is:

1. A method of making a biosensor electrode set, comprising:
    ablating through a portion of a first metallic layer with a laser, to form an interlacing electrode pattern;
    wherein said first metallic layer is on a flexible insulating substrate.

2. The method of claim 1, wherein said first metallic layer comprises copper.

3. The method of claim 1, wherein said first metallic layer comprises at least one member selected from the group consisting of gold, platinum, palladium and iridium.

4. The method of claim 1, wherein said insulating substrate is a polymer.

5. The method of claim 4, wherein said pattern has a feature size of less than 100 $\mu$m.

6. The method of claim 1, wherein said pattern has a feature size of less than 75 $\mu$m.

7. The method of claim 1, wherein said pattern has a feature size of 1 $\mu$m to 50 $\mu$m.

8. The method of claim 4, wherein said first metallic layer is in contact with said insulating substrate.

9. The method of claim 8, wherein said first metallic layer comprises at least one member selected from the group consisting of gold, platinum, palladium and iridium.

10. A method of making a sensor strip, comprising:
    forming an electrode set by the method of claim 1; and
    cutting said substrate, to form a strip.

11. The method of claim 10, further comprising applying a dielectric on a portion of said metallic layer.

12. The method of claim 11, further comprising applying a reagent on a portion of said electrode set.

13. A method of making a biosensor electrode set, comprising:
    ablating through a portion of a first metallic layer with a laser to form an interlacing electrode pattern;
    wherein said first metallic layer is on a flexible insulating substrate; and
    applying a second metallic layer on said first metallic layer.

14. The method of claim 13 wherein said first metallic layer comprises copper.

15. The method of claim 13 wherein said first metallic layer comprises at least one member selected from the group consisting of gold, platinum, palladium and iridium.

16. The method of claim 13 wherein said insulating substrate is a polymer.

17. The method of claim 13 wherein said pattern has a feature size of less than 100 µm.

18. The method of claim 13 wherein said pattern has a feature size of less than 75 µm.

19. The method of claim 13 wherein said pattern has a feature size of 1 µm to 50 µm.

20. The method of claim 16 wherein said first metallic layer is in contact with said insulating substrate.

21. The method of claim 20 wherein said first metallic layer comprises at least one member selected from the group consisting of gold, platinum, palladium and iridium.

22. A method of making a sensor strip, comprising:
forming an electrode set by the method of claim 13; and
cutting said substrate, to form a strip.

23. The method of claim 22 further comprising applying a dielectric on a portion of said metallic layer.

24. The method of claim 23 further comprising applying a reagent on a portion of said electrode set.

25. A method of making a biosensor electrode set ribbon, comprising:

ablating through a portion of a first metallic layer with a laser, to form a plurality of interlacing electrode patterns;
wherein said first metallic layer is on a flexible insulating substrate, and
said electrode set ribbon comprises a plurality of electrode sets.

26. The method of claim 25, wherein said first metallic layer comprises at least one member selected from the group consisting of gold, platinum, palladium and iridium,
said insulating substrate is a polymer, and
said first metallic layer is in contact with said insulating substrate.

27. A method of making a sensor strip, comprising:
forming an electrode set ribbon by the method of claim 25; and
cutting said ribbon into a plurality of strips;
wherein each of said strips comprises at least one of said electrode sets.

28. The method of claim 27, further comprising applying a dielectric on a portion of said metallic layer.

29. The method of claim 28, further comprising applying a reagent on a portion of said electrode set.

* * * * *